United States Patent
Inoue et al.

(10) Patent No.: US 9,897,570 B2
(45) Date of Patent: Feb. 20, 2018

(54) DISSOLVED OXYGEN MEASUREMENT SYSTEM AND METHOD OF CALIBRATING DISSOLVED OXYGEN METER

(71) Applicant: HORIBA ADVANCED TECHNO, Co., Ltd., Kyoto-shi, Kyoto (JP)

(72) Inventors: Kentaro Inoue, Kyoto (JP); Riichiro Suzuki, Kyoto (JP)

(73) Assignee: HORIBA ADVANCED TECHNO, Co., Ltd., Kyoto-shi, Kyoto (JP)

( * ) Notice: Subject to any disclaimer, the term of this patent is extended or adjusted under 35 U.S.C. 154(b) by 0 days.

(21) Appl. No.: 14/896,335

(22) PCT Filed: Aug. 7, 2014

(86) PCT No.: PCT/JP2014/070876
§ 371 (c)(1),
(2) Date: Dec. 4, 2015

(87) PCT Pub. No.: WO2015/025724
PCT Pub. Date: Feb. 26, 2015

(65) Prior Publication Data
US 2016/0131614 A1    May 12, 2016

(30) Foreign Application Priority Data
Aug. 22, 2013  (JP) ................................ 2013-171843

(51) Int. Cl.
*G01N 27/416* (2006.01)
*G01N 27/404* (2006.01)

(52) U.S. Cl.
CPC ....... *G01N 27/4162* (2013.01); *G01N 27/404* (2013.01); *G01N 27/4163* (2013.01)

(58) Field of Classification Search
CPC ............ G01N 27/4162; G01N 27/404; G01N 27/4163
(Continued)

(56) References Cited

U.S. PATENT DOCUMENTS

| 4,539,092 A | * | 9/1985 | Morgan | ............... G01N 27/404 204/403.06 |
| 5,080,865 A | * | 1/1992 | Leiner | ....................... G01N 1/28 204/401 |

(Continued)

FOREIGN PATENT DOCUMENTS

| DE | 102009039183 A1 | * | 3/2011 | ........... G01N 27/407 |
| EP | 0493819 A1 | * | 7/1992 | ......... G01N 33/1886 |

(Continued)

OTHER PUBLICATIONS

4600 Series Operating Instructions: Models 4640 and 4645 Dissolved Oxygen Analyzers. ABB Inc., 2002.*
(Continued)

*Primary Examiner* — Harshad R Patel
*Assistant Examiner* — Punam Roy
(74) *Attorney, Agent, or Firm* — Alleman Hall Creasman & Tuttle LLP

(57) ABSTRACT

In order to improve measurement accuracy by accurately calibrating sensitivity of a dissolved oxygen meter without impairing easiness in calibration, the present invention includes a dissolved oxygen measuring device that includes a cell to be loaded with a sample solution, and a dissolved oxygen meter that is attached to the cell and measures an oxygen concentration in the sample solution; and a mode switching mechanism to switch between a measurement mode, in which a sensor surface of the dissolved oxygen meter is substantially in contact with the sample solution in the cell, and a calibration mode, in which the sensor surface is substantially not in contact with the sample solution in the cell, by feeding air into the cell through a feed port disposed on the cell, and by discharging part of the sample solution through a discharge port disposed on the cell.

8 Claims, 4 Drawing Sheets

(58) Field of Classification Search
USPC .................................... 73/1.02, 1.06, 1.07
See application file for complete search history.

(56) References Cited

U.S. PATENT DOCUMENTS

| | | | | |
|---|---|---|---|---|
| 5,233,860 | A * | 8/1993 | Mori | G01N 33/1886 436/8 |
| 5,351,563 | A * | 10/1994 | Karpf | G01N 21/05 204/409 |
| 6,330,819 | B1 * | 12/2001 | Yang | G01N 33/1806 73/1.03 |
| 7,640,784 | B2 * | 1/2010 | Feng | G01N 33/1806 73/1.06 |
| 9,034,572 | B2 * | 5/2015 | Loebbert | C12M 23/28 435/287.1 |
| 2008/0067065 | A1 * | 3/2008 | Feng | G01N 33/1806 204/415 |
| 2014/0360245 | A1 * | 12/2014 | Oberlin | G01N 33/0006 73/1.06 |

FOREIGN PATENT DOCUMENTS

| | | | |
|---|---|---|---|
| JP | 57160056 | A * | 10/1982 |
| JP | 60189846 | U | 12/1985 |
| JP | 02293658 | A | 12/1990 |
| JP | 04249765 | A | 9/1992 |
| JP | 06242057 | A * | 9/1994 |
| JP | 09089873 | A | 4/1997 |

OTHER PUBLICATIONS

Tech Note 497 Detail: Dissolved Oxygen Probe Care. Pasco Scientific. Jun. 12, 2012. Accessed online on Jul. 6, 2017 at <https://www.pasco.com/support/technical-support/technote/techIDlookup.cfm?TechNoteID=497>.*

ISA Japanese Patent Office, International Search Report of PCT/JP2014/070876, dated Nov. 11, 2014, WIPO, 7 pages.

* cited by examiner

DISSOLVED OXYGEN MEASUREMENT SYSTEM AND METHOD OF CALIBRATING DISSOLVED OXYGEN METER

TECHNICAL FIELD

The present invention relates to a dissolved oxygen measurement system for measuring, for example, partial pressure of oxygen (oxygen concentration) in a sample solution, and to a method of calibrating a dissolved oxygen meter.

BACKGROUND ART

In one known dissolved oxygen meter of this type, the dissolved oxygen meter is attached to a cell, to be loaded with a sample solution, and measures partial pressure of oxygen (oxygen concentration) in the sample solution, with a sensor surface of the dissolved oxygen meter being in contact with the sample solution.

When calibrating sensitivity of said dissolved oxygen meter, as described in Patent document 1 and Patent document 2, the dissolved oxygen meter is lifted out of the sample solution to the air. The dissolved oxygen meter is then subjected to a span calibration by using the partial pressure of oxygen (oxygen concentration) in the air as a reference value.

The above calibration method is easy to conduct. However, when a partial pressure of water vapor in the air is changed due to, for example, temperature and moisture, the partial pressure of oxygen (oxygen concentration) in the air is changed accordingly. Consequently, the reference value may vary, and fail to ensure accurate calibration.

Furthermore, depending on the measurement site, it can be difficult to pull the dissolved oxygen meter out of the cell. It can therefore be difficult to use the above calibration method at some measurement sites.

RELATED ART DOCUMENTS

Patent Documents
    Patent document 1: Japanese Unexamined Patent Application Publication No. JP04-249765A; and
    Patent document 2: Japanese Unexamined Patent Application Publication No. JP06-242057A

SUMMARY OF THE INVENTION

Problems to be Solved by the Invention

The present invention has been made to solve the above described problems. The main objective of the invention is to improve measurement accuracy by accurately calibrating the sensitivity of the dissolved oxygen meter without impairing ease of calibration.

Means for Solving the Problems

That is, a dissolved oxygen measurement system includes: a dissolved oxygen measuring device having a cell to be loaded with a sample solution, and a dissolved oxygen meter that is attached to the cell and measures a oxygen concentration in the sample solution; and a mode switching mechanism to switch between a measurement mode, in which a sensor surface of the dissolved oxygen meter is in contact with the sample solution in the cell, and a calibration mode, in which the sensor surface is not in contact with the sample solution in the cell, by feeding air into the cell through a feed port disposed on the cell, and by discharging part of the sample solution through a discharge port disposed on the cell.

Herein, the phrase "the sensor surface is in contact with the sample solution in the cell" means a state in which the sensor surface is substantially in contact with the sample solution, to the extent that the accuracy required for measurement is not affected. This includes a state in which a portion of the sensor surface is not in contact with the sample solution, or a state in which an air bubble is attached to the sensor surface. Herein, the phrase "the sensor surface is not in contact with the sample solution in the cell" means a state in which the sensor surface is substantially not in contact with the sample solution to the extent that the accuracy required for calibration is not affected. This includes a state in which a portion of the sensor surface is in contact with the sample solution, or a state in which a liquid drop is attached to the sensor surface.

In the above described dissolved oxygen measurement system, part of the sample solution remains in the cell during the calibration. Therefore, the air fed into the cell is brought to a state in which it is saturated with water vapor. When the air reaches this state, the partial pressure of the water vapor becomes constant. Consequently, the partial pressure of oxygen (oxygen concentration) of the air in the cell, that is used in calibration, does not change. This makes it possible to accurately calibrate the sensitivity of the dissolved oxygen meter, thus leading to improvement in measurement accuracy. It is not necessary to pull the dissolved oxygen meter out of the cell when carrying out the calibration, and the calibration is carried out using the air without using a special gas for calibration. As a result, ease of calibration is not impaired.

In order to quickly bring the air fed into the cell to a state in which the air is saturated with water vapor when being switched from the measurement mode to the calibration mode, it is preferable that the feed port is disposed at a position that is below a surface of the sample solution in the measurement mode, and air is fed into the cell and bubbled into the sample solution.

In order to allow part of the sample solution to surely remain in the cell when being switched from the measurement mode to the calibration mode, the discharge port is preferably disposed at a position that is above an internal bottom surface of the cell.

To simplify the structure of the dissolved oxygen measurement system, it is preferable that the feed port also be used for feeding the sample solution into the cell.

To easily achieve zero point calibration without pulling the dissolved oxygen meter out of the cell, an oxygen-free gas can preferably be supplied into the cell through the feed port.

If the dissolved oxygen meter is attached to the cell such that the sensor surface is not horizontal, the sensor surface is perpendicular or inclined. With this configuration, an air bubble attached to the sensor surface in the measuring mode, or a liquid drop attached to the sensor surface in the calibration mode, are apt to separate from the sensor surface. Consequently, a measurement error due to an air bubble or a liquid drop, is less apt to occur.

A method of calibrating a dissolved oxygen meter according to the present invention includes performance of span calibration using air that is saturated with water vapor.

With the above method of calibrating the dissolved oxygen meter, the partial pressure of the water vapor of the air that is used in calibration does not change, and hence the partial pressure of oxygen (oxygen concentration) also remains constant. This ensures accurate calibration of the sensitivity of the dissolved oxygen meter, and results in improved measurement accuracy.

Effects of the Invention

The present invention thus configured is capable of improving the measurement accuracy by accurately calibrating the sensitivity of the dissolved oxygen meter while maintaining ease of operation in the calibration.

Figure 1:
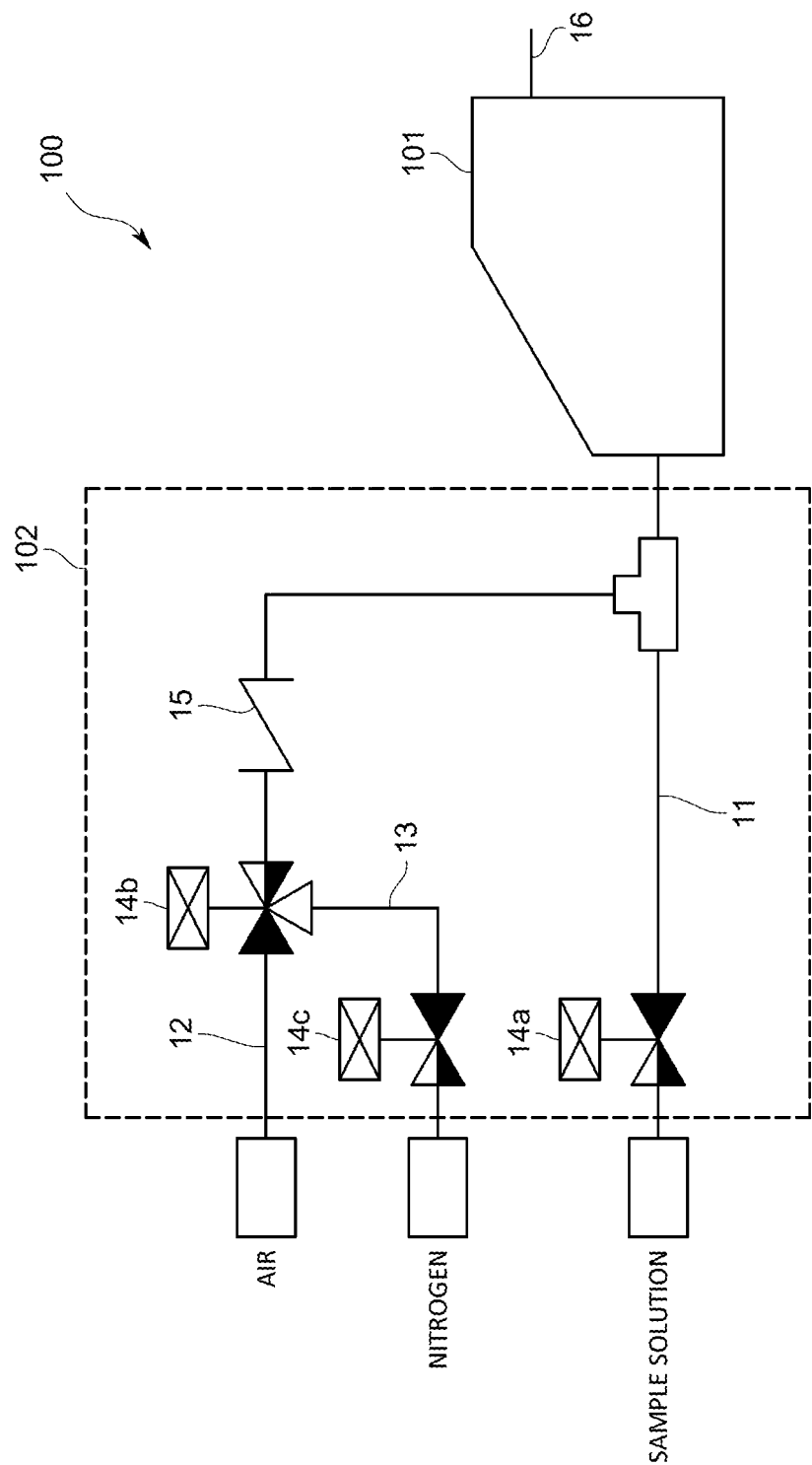
FIG. 1 is a schematic diagram showing an entire dissolved oxygen measurement system of an embodiment.

DESCRIPTION OF THE REFERENCE NUMERAL 100 dissolved oxygen measurement system
101 dissolved oxygen measuring device
102 mode switching mechanism
20 cell
S internal space
23 feed port
24 discharge port
30 dissolved oxygen meter
32 sensor surface
L solution surface

MODE FOR CARRYING OUT THE INVENTION

An embodiment of a dissolved oxygen measurement system 100 according to the present invention is described below with reference to the drawings.

As shown in FIG. 1, the dissolved oxygen measurement system 100 according to the present invention includes a dissolved oxygen measuring device 101 and a mode switching mechanism 102 to switch between a measurement mode, to measure dissolved oxygen in a sample solution, and a calibration mode, to calibrate sensitivity of a dissolved oxygen meter 30.

As shown in FIG. 1, the mode switching mechanism 102 includes a feed pipe 11 to feed a sample solution into the dissolved oxygen measuring device 101, an air pipe 12 that is connected to the feed pipe 11 and feeds air for use in a span calibration into the dissolved oxygen measuring device 101, and a nitrogen pipe 13 that is connected to the feed pipe 11 and permits feeding of nitrogen, being an oxygen-free gas for use in a zero point calibration, into the dissolved oxygen measuring device 101.

More specifically, the mode switching mechanism 102 is configured to operate by transmitting signals from a management device (not shown) to electromagnetic changeover valves 14a, 14b, and 14c, respectively disposed on the feed pipe 11, the air pipe 12, and the nitrogen pipe 13, to change over among the electromagnetic changeover valves 14a, 14b, and 14c.

Check valve 15 is disposed on the air pipe 12 and the nitrogen pipe 13 to prevent a back flow of the sample solution in the present embodiment.

The dissolved oxygen measuring device 101 is described below.

Figure 2:
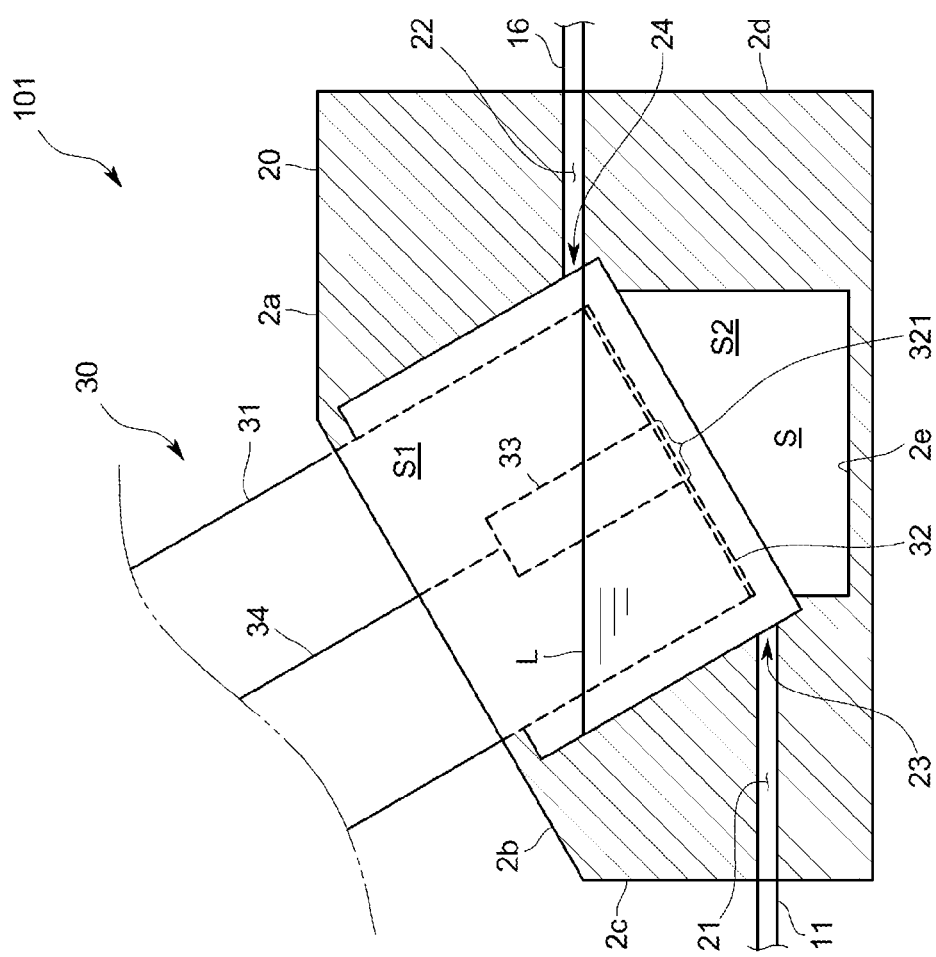
FIG. 2 is a schematic diagram showing a dissolved oxygen meter in a measurement mode of the embodiment.
Figure 3:
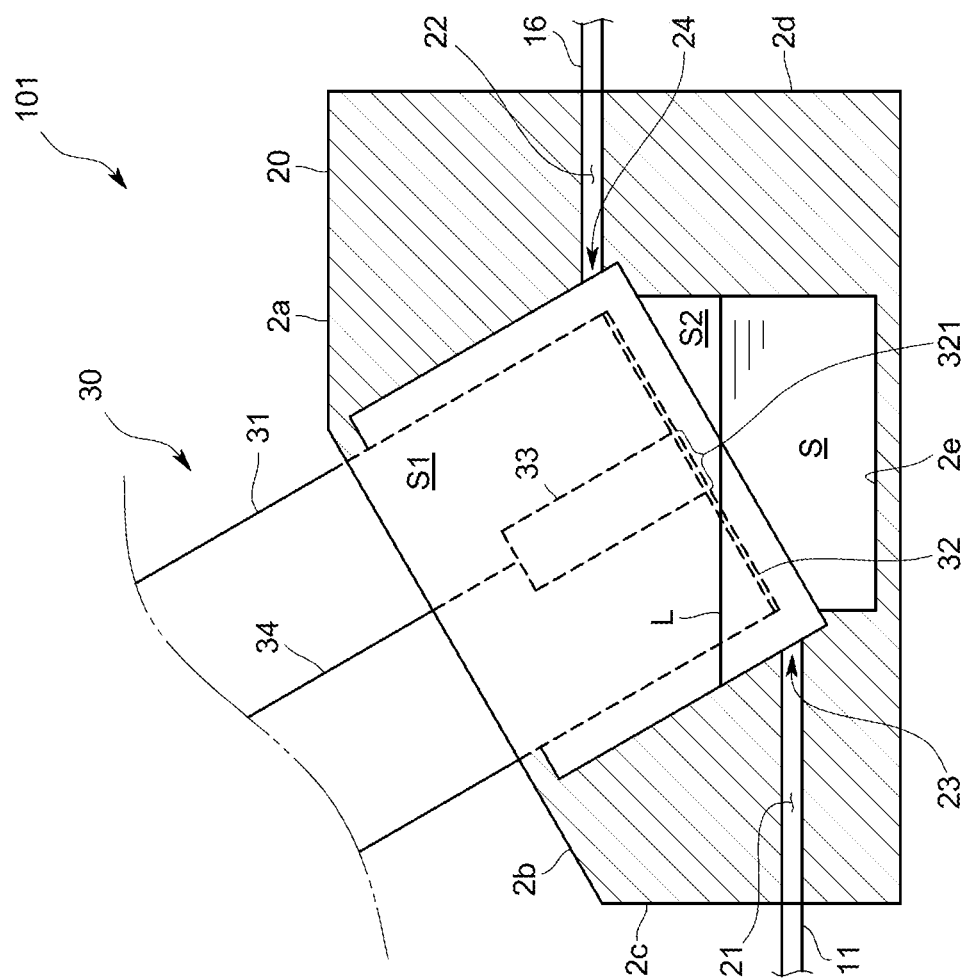
FIG. 3 is a schematic diagram showing the dissolved oxygen meter in a calibration mode of the embodiment.

As shown in FIGS. 2 and 3, the dissolved oxygen measuring device 101 is provided with the feed pipe 11 and a discharge pipe 16 to discharge of the sample solution. The dissolved oxygen measuring device 101 is a flow type dissolved oxygen measuring device that measures the partial pressure of oxygen (oxygen concentration) in the sample solution while allowing the sample solution to flow into the dissolved oxygen measuring device 101. The discharge pipe 16 communicates atmospheric pressure, therefore measurement of partial pressure of oxygen (oxygen concentration) in the sample solution is done under atmospheric pressure.

Specifically, the dissolved oxygen measuring device 101 includes a cell 20 to be loaded with the sample solution, and the dissolved oxygen meter 30 to measure the partial pressure of oxygen (oxygen concentration) in the sample solution. The dissolved oxygen meter 30 is to be inserted into the cell 20 and attached thereto in a position that is inclined away from an upright position.

As shown in FIGS. 2 and 3, the cell 20 is a block body having an inclined surface 2b extending from an upper surface 2a to one side surface 2c. The feed pipe 11 is connected to the one side surface 2c, and the discharge pipe 16 is connected to another side surface 2d.

The cell 20 includes an internal space S, to be loaded with the sample solution, a feed passage 21 to communicate between the internal space S and the feed pipe 11, and a discharge passage 22 to communicate between the internal space S and the discharge pipe 16. The feed passage 21 is disposed lower than the discharge passage 22 in the present embodiment.

The internal space S includes a first space S1 to permit insertion of the dissolved oxygen meter 30, and to communicate between the feed passage 21 and the discharge passage 22. The internal space S includes a second space S2 that is disposed below the first space S1 and extends from the first space S1 toward an internal bottom surface 2e of the cell 20.

The first space S1 has an opening formed on the inclined surface 2b of the cell 20. The first space S1 is configured so that the opening is closed with the dissolved oxygen meter 30 inserted in the first space S1.

An opening of the feed passage 21, on the internal space S side, is formed as a feed port 23, and can be used for feeding the sample solution, air, and nitrogen into the internal space S. An opening of the discharge passage 22, on the internal space S side, is formed as a discharge port 24 and can be used for discharging the sample solution, air, and nitrogen from the internal space S.

The discharge port 24 is disposed above the internal bottom surface 2e of the cell 20, and the feed port 23 is disposed below the discharge port 24 in the present embodiment.

The feed port 23 is disposed above the internal bottom surface 2e of the cell 20, and a part of the second space S2 is formed below the feed port 23 and above the internal bottom surface 2e with a dent toward the internal bottom surface 2e.

As shown in FIG. 2, the foregoing configuration ensures that when a sample solution surface L is located at a height of the discharge port 24, the feed port 23 is located below the sample solution surface L. Consequently, air and nitrogen to be fed into the internal space S through the feed port 23 are bubbled into the sample solution.

The dissolved oxygen meter 30 in the present embodiment is a diaphragm type dissolved oxygen meter. The dissolved oxygen meter 30 includes a tubular casing 31, a sensor surface 32 that is formed of an oxygen transmission film at a front end part of the casing 31, a functional electrode 33 immersed in an electrolyte loaded casing 31, and a counter electrode (not shown).

The casing 31 is inserted into the first space S1 from a direction perpendicular to the inclined surface 2b of the cell 20. By so inserting the casing 31, the sensor surface 32 is inclined relative to the horizontal position and is located below the first space S1. More specifically, the sensor surface 32 is inclined so that a region 321 of the sensor surface 32 which is opposed to the functional electrode 33 is disposed between a height at which the foregoing feed port 23 is located and a height at which the discharge port 24 is located.

The functional electrode 33 is disposed in the casing 31 so that a lead line 34 is connected to one end of the functional electrode 33 and another end thereof is adjacent to or in contact with the oxygen transmission film.

By so disposing the functional electrode 33, the oxygen in the sample solution enters the casing 31 through the sensor surface 32 and becomes reduced at the functional electrode 33. On that occasion, a current generated via the lead line 34 between the functional electrode 33 and the counter electrode (not shown) is measured with an current meter (not shown), thereby making it possible to measure the partial pressure of oxygen (oxygen concentration) in the sample solution.

The following description is of an operation of the mode switching mechanism 102 that switches between the measurement mode for measuring the partial pressure of oxygen (oxygen concentration) in the sample solution, and the calibration mode, for calibrating the sensitivity of the dissolved oxygen meter 30 in the dissolved oxygen measurement system 100.

In the measurement mode sample solution continues being fed into the internal space S by bringing the electromagnetic changeover valve 14a into an open state and the electromagnetic changeover valves 14b and 14c into a closed state. As shown in FIG. 2, in the measurement mode, the sample solution surface L is located at the height of the discharge port 24, and at least the region 321 of the sensor surface 32 of the dissolved oxygen meter 30, to which the functional electrode 33 is opposed, is in contact with the sample solution.

When the mode switching mechanism 102 switches from the measurement mode to the calibration mode, signals are respectively transmitted from the management device (not shown) to the electromagnetic changeover valves 14a, 14b, and 14c so as to bring the electromagnetic changeover valve 14a into the closed state, and also to bring either the electromagnetic changeover valve 14b or 14c into the open state, depending on the kind of calibration. More specifically, the electromagnetic changeover valve 14b is brought into the open state during the span calibration, and the electromagnetic changeover valve 14c is brought into the open state during the zero point calibration.

The following description is of the operation of a span calibration.

As described earlier, when the electromagnetic changeover valve 14b enters the open state, the air for use in the span calibration is fed through the feed port 23 into the internal space S while being bubbled into the sample solution.

Owing to the bubbling, part of the sample solution is pushed away from the sample solution surface L in the internal space S and is discharged together with the air from the internal space S through the discharge port 24. Consequently, the sample solution surface L located at the height of the discharge port 24 begins a gradual descent as the air is fed.

Subsequently, the sample solution surface L is lowered until at least the region 321 of the sensor surface 32 which is opposed to the functional electrode 33, is no longer in contact with the sample solution.

In the present embodiment, when the sample solution surface L approaches a lower end part of the region 321 of the sensor surface 32, which is opposed to the functional electrode 33, as shown in FIG. 3, a signal from the management device (not shown) brings the electromagnetic changeover valve 14b into the closed state, suspending the feed of air, thereby stopping the descent of the sample solution surface L.

Since the sample solution surface L is stopped at this position, bubbling time does not extend beyond what is necessary, and discharge of sample solution from the internal space S does not extend beyond what is necessary.

After the feed of air is suspended, the internal space S is brought to a closed state and the span calibration starts by measuring the partial pressure of oxygen (oxygen concentration) in the internal space S.

Alternatively, the span calibration may be carried out while flowing air into the internal space S in order to prevent the oxygen in the internal space S from being consumed during the span calibration.

In the present embodiment of the dissolved oxygen measurement system 100, when the mode switching mechanism 102 switches from the measurement mode to the calibration mode, the air is fed into the internal space S while being bubbled into the sample solution, and part of the sample solution remains in the internal space S. Hence, the air in the internal space S is brought to a state in which it is saturated with water vapor. Therefore in the calibration mode, a partial pressure of the water vapor in the internal space S remains constant, and accordingly a partial pressure of oxygen (oxygen concentration) does not change. The sensitivity of the dissolved oxygen meter 30 can be accurately calibrated by performing the span calibration using the partial pressure of oxygen (oxygen concentration) of the air in the internal space S as a reference value.

The air fed into the internal space S becomes saturated with water vapor. Hence in both the measurement mode and the calibration mode, it is possible to measure the partial pressure of oxygen (oxygen concentration) in a state in which the air is saturated with water vapor. This also makes it possible to accurately calibrate the sensitivity of the dissolved oxygen meter 30.

There is no need to pull the dissolved oxygen meter 30 out of the cell 20 when carrying out the calibration, and the span calibration can be performed with air, rather than with using any special gas for the span calibration. Ease of calibration is therefore ensured. Furthermore, the zero point calibration can be performed by using nitrogen instead of the air, thus making it possible to improve ease of conducting calibration.

When conducting the zero point calibration, nitrogen is fed into the internal space S while being bubbled into the sample solution. Consequently, oxygen contained in the sample solution is purged and the sample solution approaches an oxygen-free state.

The opening of the first space S1 formed on the inclined surface 2b is configured to be closed in a state where the dissolved oxygen meter 30 is inserted in the first space S1.

This makes it possible to quickly bring the air fed into the internal space S to the state in which it is saturated with water vapor.

Moreover, the portion of the second space S2 that is formed below the feed port 23, is formed as a dent toward the internal bottom surface 2e. Therefore, even when the air is vigorously fed through the feed port 23 into the internal space S, it is possible to ensure that part of the sample solution will remain in the dent of the second space S2.

The feed port 23 can be used for feeding the sample solution, air, and nitrogen into the cell 20 Feeding a sample solution, air, or nitrogen through the feed port 23 into the internal space S is conducted by changing over the electromagnetic changeover valves 14a, 14b, and 14c. This configuration contributes to simplifying the internal structure of the dissolved oxygen measuring device 101.

The dissolved oxygen meter 30 is attached to the cell 20 in a manner in which the sensor surface 32 is inclined relative to the horizontal position. Therefore, in the event that an air bubble is attached to the sensor surface 32 during the measurement mode, or in the event that a liquid drop is attached to the sensor surface 32 during the calibration mode, the liquid drop and air bubble are apt to separate from the sensor surface 32. As a result, it is possible to significantly reduce the risk of a measurement error occurring due to the presence of an air bubble or a liquid drop on the surface of the sensor.

The present invention is not limited to the foregoing embodiment.

Figure 4:
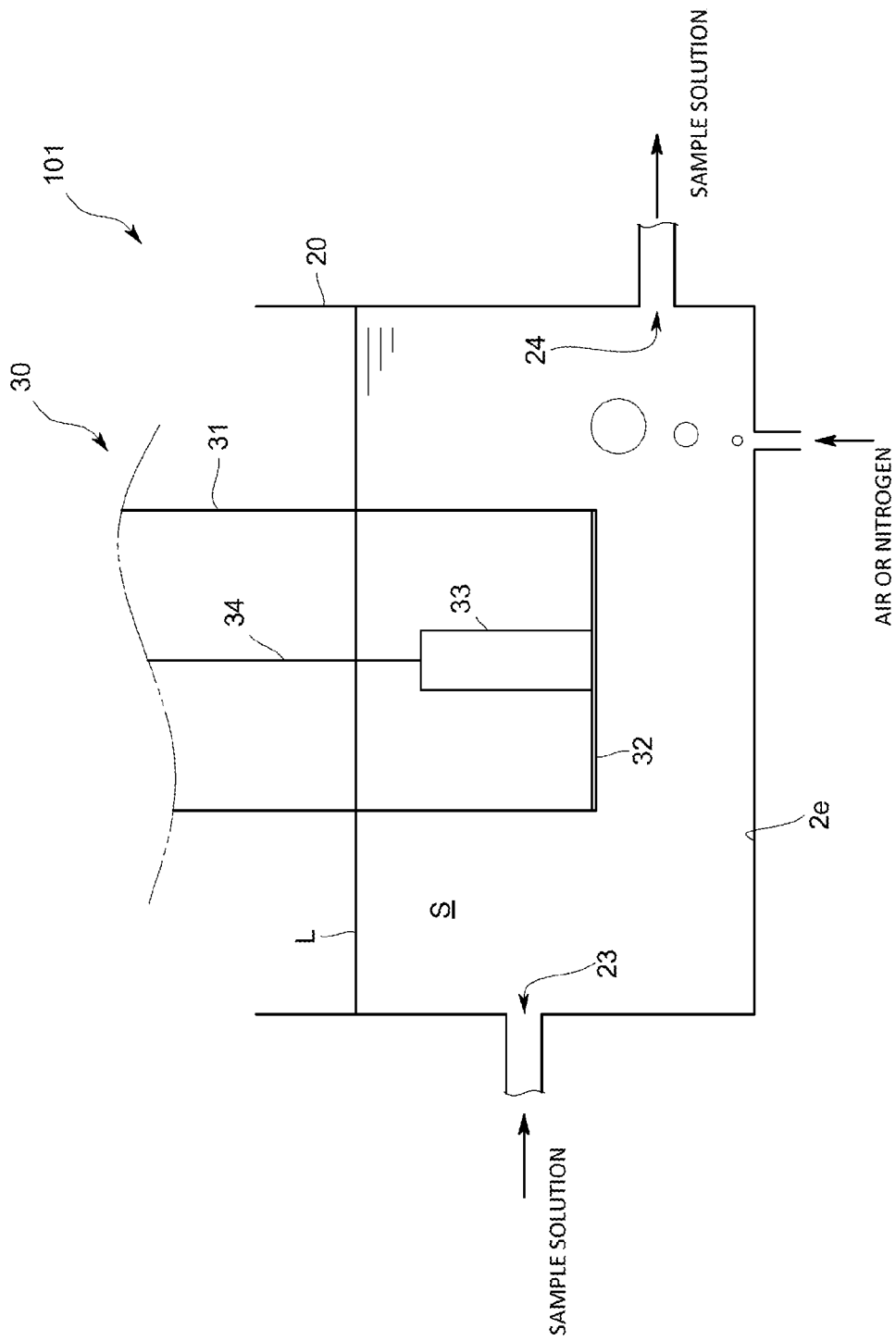
FIG. 4 is a schematic diagram showing a dissolved oxygen meter in a modified embodiment.

For example, as shown in FIG. 4, the feed port 23 which can be used for feeding a sample solution into the internal space S may be disposed above the discharge port 24, which can be used for discharging a sample solution from the internal space S.

As shown in FIG. 4, air or nitrogen may be fed, while being bubbled into a sample solution, from the internal bottom surface 2e of the cell 20 into the internal space S. The dissolved oxygen meter 30 may also be disposed in an upright position in the cell 20.

In the foregoing embodiment a single feed port can be used for feeding the sample solution, air, and nitrogen. However, a plurality of feed ports respectively configured to feed the sample solution, air, and nitrogen may also be disposed.

The dissolved oxygen meter in the present embodiment is a flow type dissolved oxygen meter. However, alternatively a batch type dissolved oxygen meter may be used. An example of a batch type dissolved oxygen meter is one which is configured to measure a partial pressure of oxygen (oxygen concentration) while stirring the sample solution loaded in the internal space by disposing, for example, a stirrer on the internal bottom surface of the cell.

Air is used for the span calibration in the foregoing embodiment. However, air may be replaced with a span calibration gas that has a known oxygen concentration. Nitrogen is used for the zero point calibration in the foregoing embodiment. However, nitrogen is replaceable with any oxygen-free gas.

The dissolved oxygen meter measures the partial pressure of oxygen (oxygen concentration) in the sample solution in the foregoing embodiment. However, the dissolved oxygen meter may measure an alternative value related to partial pressure of oxygen (oxygen concentration), such as oxygen content and activity.

The dissolved oxygen meter used in the present embodiment is a diaphragm type dissolved oxygen meter. However, alternatively a fluorescent type dissolved oxygen meter that measures partial pressure of oxygen (oxygen concentration) according to a lifetime of a fluorescent coating, may also be used.

Furthermore, instead of the dissolved oxygen meter of the foregoing embodiment, a dissolved gas meter for measuring a concentration of a gas, such as ozone or hydrogen, dissolved in the sample solution may be attached to the cell so as to measure the concentration of the gas.

When the dissolved oxygen meter is used for measuring the concentration of a gas other than oxygen, as described above, it is required, in the calibration mode, to perform a span calibration by feeding into the cell a span calibration gas with a known content rate of the gas to be measured.

With the above configuration, the span calibration gas fed into the cell becomes saturated with water vapor. Hence, in both the measurement mode and the calibration mode, it is possible to measure, for example, ozone and hydrogen in the state in which the water vapor is saturated. This makes it possible to accurately calibrate the sensitivity of the dissolved gas meter.

The present invention is not limited to the foregoing embodiments. Various modifications can be made to the present invention without departing from its spirit and scope.

INDUSTRIAL APPLICABILITY

The present invention is capable of improving measurement accuracy by accurately calibrating the sensitivity of the dissolved oxygen meter while ensuring the ease of operation during the calibration.

The invention claimed is:

1. A dissolved oxygen measurement system comprising:
a dissolved oxygen measuring device comprising a cell to be loaded with a sample solution, and a dissolved oxygen meter that is attached to the cell and measures an oxygen concentration in the sample solution; and
a mode switching mechanism to switch between a measurement mode, in which a sensor surface of the dissolved oxygen meter is in contact with the sample solution in the cell, and a calibration mode, in which the sensor surface is not in contact with the sample solution in the cell, by feeding air into the cell through a feed port disposed on the cell, and by discharging part of the sample solution through a discharge port disposed on the cell, wherein
the sensor surface is higher than the surface of the sample solution in the cell during the calibration mode.

2. The dissolved oxygen measurement system according to claim 1, wherein the feed port is disposed at a position that is below a surface of the sample solution in the measurement mode, and air is fed into the cell and bubbled into the sample solution.

3. The dissolved oxygen measurement system according to claim 1, wherein the discharge port is disposed at a position that is above an internal bottom surface of the cell.

4. The dissolved oxygen measurement system according to claim 1, wherein the feed port is used for feeding the sample solution into the cell.

5. The dissolved oxygen measurement system according to claim 1, wherein an oxygen-free gas is suppliable into the cell through the feed port.

6. The dissolved oxygen measurement system according to claim 1, wherein the dissolved oxygen meter is attached to the cell and the sensor surface is not horizontal.

7. A dissolved oxygen measuring device comprising a cell to be loaded with a sample solution, and a dissolved oxygen meter that is attached to the cell and measures an oxygen concentration in the sample solution, wherein the dissolved oxygen measuring device is used together with a mode switching mechanism to perform switching between a measurement mode, in which a sensor surface of the dissolved oxygen meter is in contact with the sample solution in the cell, and a calibration mode, in which the sensor surface is not in contact with the sample solution in the cell, by feeding air into the cell through a feed port disposed on the cell, and by discharging part of the sample solution through a discharge port disposed on the cell, wherein the sensor surface is higher than the surface of the sample solution in the cell during the calibration mode.

8. A method of calibrating a dissolved oxygen meter that is attached to a cell loaded with a sample solution to measure an oxygen concentration in the sample solution, the method comprising:

performing a span calibration using air that is saturated with water vapor, switching from a measurement mode, in which a sensor surface of the dissolved oxygen meter is in contact with the sample solution in the cell, to a calibration mode, in which the sensor surface is not in contact with the sample solution in the cell, by feeding air into the cell and by discharging part of the sample solution, and making the sensor surface of the dissolved oxygen meter to be higher than a surface of the sample solution in the cell loaded with the sample solution during the calibration mode.

* * * * *